United States Patent
Bruce et al.

(12)

(10) Patent No.: US 6,388,066 B1
(45) Date of Patent: May 14, 2002

(54) MAR/SAR ELEMENTS FLANKING RSYN7-DRIVEN CONSTRUCT

(75) Inventors: Wesley B. Bruce, Urbandale; Sheila E. Maddock, Johnston, both of IA (US)

(73) Assignee: Pioneer Hi-Bred International, Inc., Des Moines, IA (US)

( * ) Notice: Subject to any disclaimer, the term of this patent is extended or adjusted under 35 U.S.C. 154(b) by 0 days.

(21) Appl. No.: 09/405,779

(22) Filed: Sep. 27, 1999

Related U.S. Application Data

(60) Provisional application No. 60/102,288, filed on Sep. 29, 1998.

(51) Int. Cl.⁷ ............................................. C07H 21/04
(52) U.S. Cl. ................... 536/24.1; 435/320.1; 435/468; 800/278
(58) Field of Search ............................ 435/320.1, 440, 435/468; 800/278, 298; 535/23.1, 24.1

(56) References Cited

U.S. PATENT DOCUMENTS

| 5,187,267 A | | 2/1993 | Comai et al. ............... 800/298 |
| 5,888,774 A | * | 3/1999 | Delcuve |
| 6,072,050 A | * | 6/2000 | Bowen et al. |

FOREIGN PATENT DOCUMENTS

| WO | WO 94/07902 | 4/1994 |
| WO | WO 94/24293 | 10/1994 |
| WO | WO 97/27207 | 7/1997 |
| WO | WO 97/47756 | 12/1997 |

OTHER PUBLICATIONS

Kalos et al (1995) Mol. Cell. Biol. 15: 198–207.*
Avramova et al. (1993) "Isolation of Matrices From Maize Leaf Nuclei: Identification of a Matrix–Binding Site Adjacent to the Adh1 Gene", *Plant Molecular Biology* 22:1135–1143.
Avramova et al. (1995) "Matrix Attachment Regions and Transcribed Sequences Within A Long Chromosomal Continuum Containing Maize Adh1", *The Plant Cell* 7:1667–1680.
Breyne et al. (1992) "Characterization of a Plant Scaffold Attachment Region in a DNA Fragment That Normalizes Transgene Expression in Tobacco", *The Plant Cell* 4:463–471.
Forrester et al. (1994) "Dependence fo Enhancer–Mediated Transcription of the Immunoglobulin μ Gene on Nuclear Matrix Attachment Regions", *Science* 265:1221–1226.
Mlynarova et al. (1995) "The MAR–Mediated Reduction in Position Effect Can Be Uncoupled from Copy Number–Dependent Expression in Transgenic Plants", *The Plant Cell* 7:599–609.
Paul et al. (1993) "Osmium Tetroxide Footprinting of a Scaffold Attachment Region in the Maize Adhl Promoter", *Plant Molecular Biology* 22:1145–1151.
Mlynarova et al. (1995) "The MAR–Mediated Reduction in Position Effect Can Be Uncoupled from Copy Number–Dependent Expression in Transgenic Plants", *The Plant Cell* 7:599–609.

* cited by examiner

*Primary Examiner*—Remy Yucel
*Assistant Examiner*—Bronwen M. Loeb
(74) *Attorney, Agent, or Firm*—Alston & Bird LLP

(57) ABSTRACT

This invention discloses to compositions and methods for altering the characteristic pattern of expression associated with a promoter. More particularly the constitutive expression pattern associated with the small synthetic promoter, Rsyn7 is modified so that expression of a heterologous nucleotide sequence operably linked to the Rsyn7 promoter is in a tissue localized manner. This modification of the Rsyn7 pattern of expression occurs as a result of the addition of matrix attachment region DNA sequences to the flanks or 5' and 3' ends of an expression cassette comprising the Rsyn7 promoter operably linked to a heterologous nucleotide sequence of interest. DNA constructs, transformed plant cells and transformed plants are provided.

26 Claims, 3 Drawing Sheets

SEQUENCE LISTING

```
<160> NUMBER OF SEQ ID NOS: 3

<210> SEQ ID NO 1
<211> LENGTH: 72
<212> TYPE: DNA
<213> ORGANISM: Artificial Sequence
<220> FEATURE:
<223> OTHER INFORMATION: Rsyn7 Core Promoter

<400> SEQUENCE: 1
ggatccactc gagcggctat aaatacgtac ctacgcacgc tgcgctacca tcccgagcac      60
tgcagtgtcg ac                                                         72

<210> SEQ ID NO 2
<211> LENGTH: 72
<212> TYPE: DNA
<213> ORGANISM: Artificial Sequence
<220> FEATURE:
<223> OTHER INFORMATION: Modified Rsyn7 Core Promoter

<400> SEQUENCE: 2
ggatccactc gagcggctat aaatasstas stasssasss tssssstassa tcccgagcac     60 tgcagtgtcg ac                                                         72

<210> SEQ ID NO 3
<211> LENGTH: 96
<212> TYPE: DNA
```

```
-continued

<213> ORGANISM: Artificial Sequence
<220> FEATURE:
<223> OTHER INFORMATION: Rsyn7

<400> SEQUENCE: 3
ggatcctatg cgtatggtat gacgtgtgtt caagatgatg acttcaaacc tacctatgac       60
gtatggtatg acgtgtgtcg actgatgact tagatc                                 96
```

MAR/SAR ELEMENTS FLANKING RSYN7-DRIVEN CONSTRUCT

CROSS-REFERENCE

This application claims the benefit of U.S. Provisional Application Ser. No. 60/102,288, filed Sep. 29, 1998.

FIELD OF THE INVENTION

The present invention relates to genetic engineering, particularly to compositions and methods for altering the normal pattern of expression associated with a particular promoter-driven construct in plants using nuclear matrix attachment regions.

BACKGROUND OF THE INVENTION

Extensive literature exists on the potential role of matrix attachment region (MAR) DNA sequences in the regulation of eukaryotic gene expression (see, for example, Mirkovitch et al. (1984) Cell 39:223–232; Stief et al. (1989) Nature 341:343–345; Bode et al. (1992) Science 255:195–197; Spiker and Thompson (1996) Plant Physiol. 110:15–21). MAR sequences (also called scaffold attachment region, or SAR, sequences) are examples of elements that are thought to play a role in the regulation of transcription. Early work established that MAR sequences must be incorporated into the host genome to have their effect (Stief et al. (1989) Nature 341:343–345). These regions of highly AT-rich DNA (more than 70%) have been shown to increase transgene expression in stably transformed animal cell lines (see, for example Stief et al. (1989) Nature 341:343–345; Phi-Van et al. (1990) Mol. Cell. Biol. 10:2302–2307; Klehr and Bode (1991) Biochemistry 30:1264–1270; Poljak et al. (1994) Nucleic Acids Res. 22:4386–4394; Kalos and Fournier (1995) Mol. Cell. Biol. 15:198–207) and transformed plants (see, for example, van der Geest et al. (1994) Plant J. 6:413–423; Schöffl et al. (1993) Transgenic Res. 2:93–100; Allen et al. (1993) Plant Cell 5:603–613; Mlynárová et al. (1994) Plant Cell 6:417–426 and (1995) Plant Cell 7:599–609; and Spiker et al. (1995) J. Cell Biochem. 21B: 167). Decreased transformant-to-transformant variability in expression with the use of MAR sequences has been reported less frequently (see Stief et al. (1989) Nature 341:343–345; Breyne et al. (1992) Plant Cell 4:463–471; van der Geest et al. (1994) Plant J. 6:413–423; Mlynárováet al. (1994) Plant Cell 6:417–426). This position-independent expression has been attributed to insulation of foreign DNA inserts from position effects, possibly by protecting the DNA insert from interfering effects of adjacent chromatin enhancers or silencers, or by inhibiting methylation. Additionally, copy-number dependence (i.e., increased levels of expression with increased copies of the transgene) with the use of MAR sequences has been infrequently reported for transformed animal cell lines (see Stief et al. (1989) Nature 341:343–345) and transformed plants (vander Geest et al. (1994) Plant J. 6:413–423).

MAR sequences serve to attach chromatin loop domains to the nuclear matrix fiber, forming the boundaries for these DNA loops (Gasser et al. (1989) Int. Rev. Cytol. 119:57–96; Laemmil et al. (1992) Curr. Opin. Genet. Dev. 2:275–285; Dorer and Henikoff(1994) Cell 77:993–1002). Their exact role in eukaryotic gene expression is not known, though several hypotheses have been proposed. Early models suggested that incorporation of foreign DNA into the host genome occurs randomly in the absence of MAR sequences. Hence, if incorporation occurs within a transcriptionally inactive chromatin domain, the foreign DNA takes on an inactive chromatin structure, thus reducing the potential for transcription of the foreign DNA. If incorporation occurs within a transcriptionally active chromatin domain, the transgene takes on the active chromatin structure, thus increasing the potential for transcription of that DNA. If the foreign DNA is flanked by MAR sequences, however, incorporation into an active or inactive region results in the formation of an independent domain, which itself may assume an active or inactive chromatin state.

The functional importance of the independent domain is that the foreign DNA insert is isolated from the effects of the chromatin around it, hence contributing to the suppression of gene silencing and position effects, and overall enhancement of expression. This model is oversimplified, however, as it cannot explain persistent variation in expression of low-copy transformants and inconsistencies in copy number-dependent transgene expression (see Spiker and Thompson (1996) Plant Physiol. 110: 15–21).

Others have proposed that MAR sequences form nucleation points for DNA unwinding (Bode et al. (1992) Science 225:195–197); that MAR sequences form sites of nucleation for HMG proteins to displace H1 histones, allowing highly coiled chromatin fibers to unwind (Kas et al. (1993) EMBO J. 12:115–126); that MAR sequences stabilize chromosomal topology arising as a consequence of hyperacetylation of histone cores (Schlake et al. (1994) Biochemistry 33:4197–4206); and that MAR sequences stimulate transgene expression by reducing the severity of homology-dependent gene silencing (Spiker and Thompson (1996) Plant Physiol. 110:15–21).

To date the predominant investigatory focus has been on the use of MAR sequences to enhance transgene expression. Little is known about other potential roles for those sequences such as their ability to alter normal patterns of expression. Such changes might include a modification of expression so that, when a transgene is operably linked to a promoter with a characteristic pattern of expression (i.e. constitutive) the addition of MAR elements alters this pattern of expression, generating a promoter that drives expression in a tissue-preferred or tissue localized manner.

Expression of heterologous DNA sequences in a plant host is dependent upon the presence of an operably linked promoter that is functional within the plant host. Choice of the promoter sequence will determine when and where within the organism the heterologous DNA sequence is expressed. When continuous expression is desired throughout the cells of a plant, constitutive promoters are utilized. In contrast, when gene expression in response to a stimulus is desired, inducible promoters are the regulatory element of choice. When expression in specific tissues or organs are desired, tissue-preferred promoters may be used.

While a number of promoters are readily available and are frequently used in research involving recombinant DNA technology, these promoters are primarily limited to their native functional character or pattern of expression, i.e., constitutive, inducible, etc. Methods by which these promoters, or the pattern of expression exhibited by these promoters can be manipulated to generate an altogether different pattern of expression have thus far been unreliable. There is great value in the ability to manipulate the expression pattern of any promoter by simply genetically engineering into it the capacity to express a coding sequence behind its control in a wholly different manner. Thus, this invention is drawn to the use of nuclear matrix attachment regions (MAR) DNA sequences to alter the normal pattern of expression associated with a particular promoter-driven construct and thereby generating a promoter capable of driving expression of a heterologous nucleotide sequence in a manner which satisfies the needs of an individual investigator.

SUMMARY OF THE INVENTION

A DNA construct comprising matrix attachment region (MAR) sequences having altered expression patterns is provided. The invention further encompasses a method of altering the characteristic expression pattern associated with a promoter-driven construct by using MAR sequences.

One aspect of the present invention is a DNA construct comprising an expression cassette having, in the 5'-to-3' direction, a nucleotide sequence or gene of interest operably linked to the transcription initiation region or promoter, a transcription and translation termination region, and a matrix attachment region DNA sequence positioned either 5' to the transcription initiation region, 3' to the termination region, or in both 3' and 5' positions. Preferably, the expression cassette is flanked by the MAR DNA sequences positioned both 5' to the transcription initiation region and 3' to the termination region. This DNA construct may be assembled within the backbone of any conventional vector.

A second aspect of the present invention is a method for modifying or altering the characteristic expression patterns associated with a particular promoter-driven construct in plants by flanking the construct with at least one matrix attachment region (MAR) DNA sequence. This method comprises transforming a regenerative plant cell with the DNA construct of this invention using conventional transformation methods known in the art. More preferably the method comprises altering the native constitutive expression pattern of a promoter-driven construct to exhibit or be capable of expression in a tissue localized manner. Even more preferably the promoter-driven construct whose expression is altered comprises the small synthetic promoter, Rsyn7.

The present invention also provides for stably transformed plants, which comprise the DNA construct according to the invention, that exhibit tissue localized expression of a heterologous nucleotide sequence as a result of the attachment of the MAR DNA sequences to the 5' and 3' ends of the construct. Seeds of such plants are also provided.

DETAILED DESCRIPTION OF THE INVENTION

Figure 1:
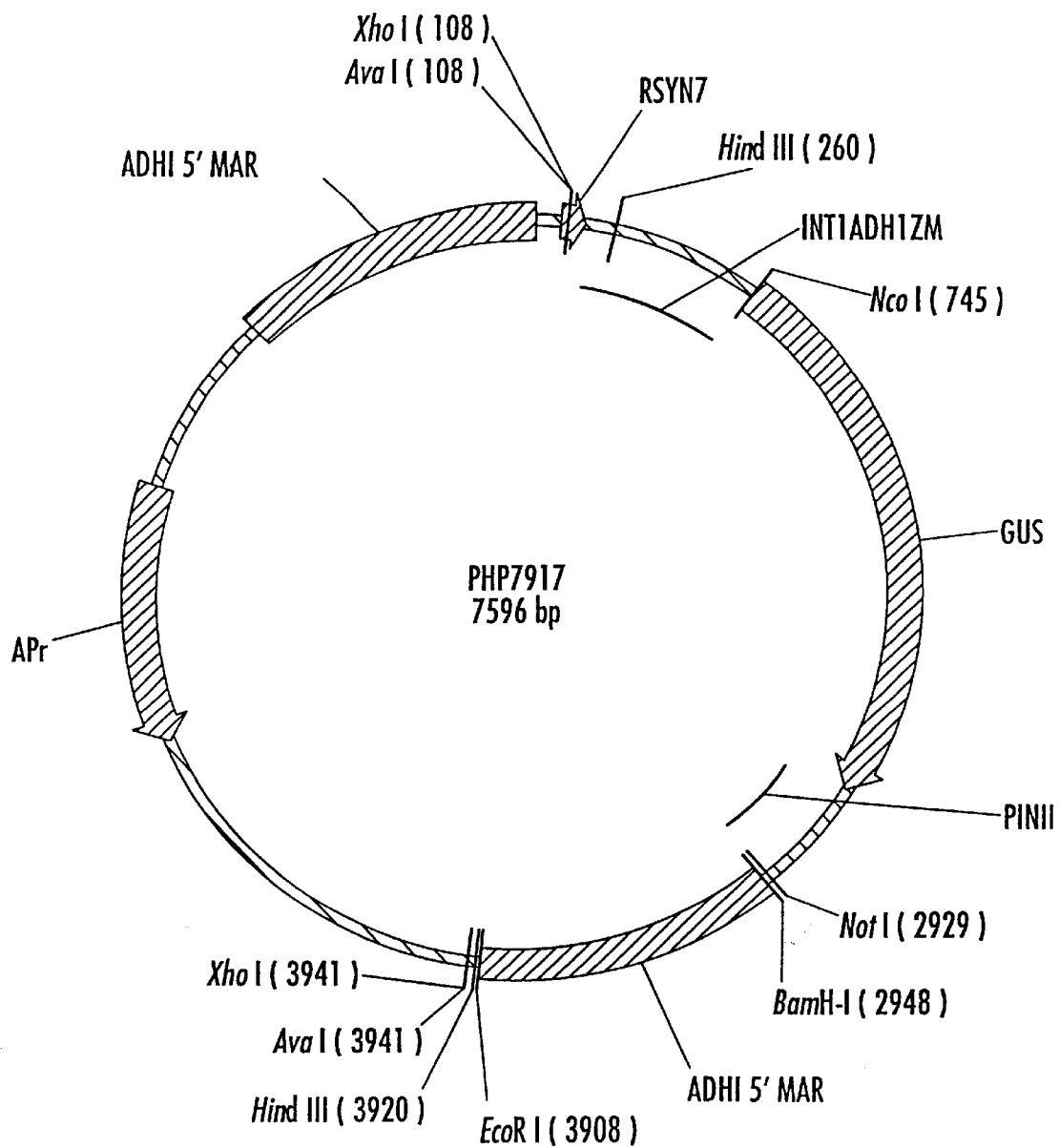
FIG. 1 schematically illustrates the plasmid comprising the DNA construct with its expression cassette flanked by maize matrix attachment regions according to the present invention. This plasmid also contains the maize AdhI-intron 1 designated as INTADH1ZM. The abbreviation are as follows: GUS (β-glucuronidase); PINII (proteinase inhibitor of potato typeII terminator); TA Perox (*Triticus aestivum* peroxidate promoter); Ap$^r$ (ampicillin resistance).

The present invention is drawn to a method and compositions for modifying or altering the characteristic expression patterns associated with a promoter-driven construct thereby controlling the expression of a heterologous nucleotide sequence operably linked to the promoter. This is accomplished by flanking a promoter-driven construct with matrix attachment region (MAR) DNA sequences prior to transfer to a plant host. The construct may be flanked at either, or both, the 5' and 3' ends of the construct.

The present invention provides a method wherein the expression of a coding sequence is altered so that expression patterns of the coding sequence operably linked to a promoter are modified. In one example, a constitutive expression pattern associated with a promoter-driven construct is altered so that expression of a heterologous nucleotide sequence upon addition of flanking MAR sequences to the DNA construct becomes tissue localized. For the purposes of the invention "tissue localized expression" is intended as expression only in specific tissues of the plant. For example, a heterologous nucleotide sequence operably linked to the small synthetic promoter, Rsyn7 has been altered from a constitutive pattern of expression to expression only in specific tissues within the plant. In particular, for Rsyn7 driven constructs, expression has been localized in the lateral root emergence site, the glumes surrounding developing kernels, and the palea/lemma of tassels of maize.

The coding sequence may be native or heterologous to the promoter. By "heterologous" is intended a sequence that is not naturally occurring with the promoter sequence. While this nucleotide sequence is heterologous to the promoter sequence it may be homologous, or native, or heterologous, or foreign, to the plant host.

By "matrix attachment region" is intended a DNA sequence comprising about 100 to 1,000 bp, preferably about 200 to 700 bp more preferably about 300 to 500 bp, that putatively attaches transcriptionally active DNA loop domains to the proteinaceous network of filaments known as the nuclear matrix (Pienta et al. (1991) *Crit. Rev. Eukaryotic Gene Express.* 1:355–385; Laemmil et al. (1992) *Curr. Opin. Genet. Dev.* 2:275–285). By operational definition, MAR DNA sequences are isolated DNA fragments that bind to purified nuclear matrices, either by occupying free sites or by displacing resident MARs. A number of MAR sequences from plant or animal sources have been identified and are known in the art (for example, yeast and tobacco (Allen et al. (1993) *Plant Cell* 5:603–613; Spiker et al. (1995) *J. Cell Biochem.* 21B:167); tobacco (Breyne et al. (1992) *Plant Cell* 4:463–471; Hall et al. (1991) *Proc. Natl. Acad. Sci. USA* 88:9320–9324); soybean heat shock gene (Schöffl et al. (1993) *Transgenic Res.* 2:93–100); bean phaseolin gene (van der Geest et al. (1994) *Plant J.* 6:413–423); and chicken lysozyme gene (Stief et al. (1989) *Nature* 341:343–345); Phi-Van et al. (1990) *Mol. Cell. Biol.* 10:2302–2307; Mlyn árováetal. (1995) *Plant Cell* 7:599–609). Any of these MAR DNA sequences can be used in the present invention. More preferably, a strong MAR sequence will be used. By strong MAR sequence is intended an isolated end-labeled DNA fragment whose binding affinity for the purified, insoluble nuclear matrix of the plant host cells during an incubation period is greater than that of other similarly isolated end-labeled DNA fragments, such that following centrifugation of the co-incubated nuclear material, it is found almost entirely within the insoluble pellet fraction along with the nuclear matrix. This contrasts with weaker MAR sequences, whose lesser affinity for the insoluble nuclear matrix results in a much smaller proportion of the end-labeled DNA fragment residing in the insoluble pellet fraction. Any identified strong MAR may be used in the present invention, more preferably the strong MAR is a maize MAR, more particularly the maize MAR from the maize ADH1 gene identified by Azramova et al. (1993) (*Plant Mol. Biol.* 22:1135–1143). For the purposes of the present invention, the MAR sequence of choice is incorporated into a DNA construct containing a promoter operably linked to a heterologous nucleotide sequence of interest.

Fragments and variants of MAR nucleotide sequences are encompassed by the present invention. By "fragment" is intended a portion of the nucleotide sequence. Fragments of a MAR nucleotide sequence may retain biological activity and hence bind to purified nuclear matrices and/or alter the expression patterns of coding sequences operably linked to a promoter. Fragments of a MAR nucleotide sequence may range from at least about 100 to 1,000 bp, about 200 to 700 bp, more preferably about 300 to 500 bp nucleotides, or up to the number of nucleotides present in a full-length MAR.

By "variants" is intended substantially similar sequences. Variant nucleotide sequences also include synthetically derived nucleotide sequences, such as those generated, for example, by using site-directed mutagenesis. Generally, variants of a particular nucleotide sequence of the invention will have at least 50%, 60%, 70%, generally at least 75%, 80%, 85%, preferably about 90% to 95% or more, and more preferably about 98% or more sequence identity to that particular nucleotide sequence as determined by sequence alignment programs described elsewhere herein using default parameters.

Methods of alignment of sequences for comparison are well known in the art. Thus, the determination of percent sequence identity between any two sequences can be accomplished using a mathematical algorithm. Preferred, non-limiting examples of such mathematical algorithms are the algorithm of Myers and Miller (1988) *CABIOS* 4:11–17; the local homology algorithm of Smith et al. (1981) *Adv. Appl. Math.* 2:482; the homology alignment algorithm of Needleman and Wunsch (1970) *J. Mol. Biol.* 48:443–453; the search-for-similarity-method of Pearson and Lipman (1988) *Proc. Natl. Acad. Sci.* 85:2444–2448; the algorithm of Karlin and Altschul (1990) *Proc. Natl. Acad. Sci. USA* 872264, modified as in Karlin and Altschul (1993) *Proc. Natl. Acad. Sci. USA* 90:5873–5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. (1988) *Gene* 73:237–244 (1988); Higgins et al. (1989) *CABIOS* 5:151–153; Corpet et al. (1988) *Nucleic Acids Res.* 16:10881–90; Huang et al. (1992) *CABIOS* 8:155–65; and Pearson et al. (1994) *Meth. Mol. Biol.* 24:307–331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See http://www.ncbi.nlm.nih.gov. Alignment may also be performed manually by inspection.

For purposes of the present invention, comparison of nucleotide or protein sequences for determination of percent sequence identity to a MAR sequences is preferably made using the Clustal W program (Version 1.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

Another indication that nucleotide sequences are substantially identical is if two molecules hybridize to each other under stringent conditions. Generally, stringent conditions are selected to be about 5° C. lower than the thermal melting point for the specific sequence at a defined ionic strength and pH. However, stringent conditions encompass temperatures in the range of about 1° C. to about 20° C. depending upon the desired degree of stringency as otherwise qualified herein.

Any promoter, whether naturally occurring or synthetically produced, may be used to drive the coding sequence, so long as the addition of the MAR elements leads to an altered pattern of expression. Having recognized that MAR elements in combination with a promoter may change expression patterns of the coding sequence under the control of the promoter, other promoters and MAR elements can be tested. Of particular interest is the Rsyn7 promoter, a small synthetic promoter. In conjunction with flanking matrix attachment region (MAR) DNA sequences, the characteristic expression pattern associated with an Rsyn7 promoter-driven construct is modified.

The Rsyn7 promoter is described PCT Application Ser. No. U.S. 99/03863, herein incorporated by reference. The Rsyn7 core promoter comprises a TATA motif and a GC rich "TATA to start of transcription" region having 64% or greater GC content (SEQ ID NOs: 1 and 2). A novel upstream element, SEQ ID NO:3, helps to potentiate transcription. The promoter when placed 5' and operably linked to a structural gene promotes constitutive expression that is non-tissue-preferred in transgenic plants (SEQ ID NOs:1, 2, and 3).

The matrix attachment region (MAR) DNA sequences are a part of a DNA construct that comprises the Rsyn7 promoter operably linked to a heterologous nucleotide sequence of interest. The MAR sequences may be placed at the 5', the 3', or more preferably located at both the 5' and the 3' ends of the DNA construct, effectively flanking the construct.

Other promoter regions useful for the purposes of this invention may be isolated and tested for altered expression patterns. The promoter sequences used in the promoter-driven constructs of this invention can be modified to provide for a range of expression levels of the heterologous nucleotide sequence. Thus, less than the entire promoter regions may be utilized and the ability to drive tissue localized expression retained. However, it is recognized that expression levels of mRNA may be decreased with deletions of portions of the promoter sequences. Generally, at least about 20 nucleotides of a promoter sequence will be used to drive expression of a nucleotide sequence.

It is recognized that to increase transcription levels enhancers may be utilized in combination with the promoter regions used in the promoter-driven constructs of the invention. Enhancers are nucleotide sequences that act to increase the expression of a promoter region. Enhancers are known in the art and include the SV40 enhancer region, the 35S enhancer element, and the like.

Modifications of the promoter sequences used in the promoter-driven constructs can provide for a range of expression of the heterologous nucleotide sequence. Thus, they may be modified to be weak promoters or strong promoters. Generally, by "weak promoter" is intended a promoter that drives expression of a coding sequence at a low level. By "low level" is intended at levels of about 1/10,000 transcripts to about 1/100,000 transcripts to about 1/500,000 transcripts. Conversely, a strong promoter drives expression of a coding sequence at a high level, or at about 1/10 transcripts to about 1/100 transcripts to about 1/1,000 transcripts.

The coding sequence operably linked to a promoter to make up the promoter-driven construct may be used for varying the phenotype of the plants more particularly, specific tissues or organs within the plant, even more particularly the lateral root emergence sites, the glumes surrounding developing kernels, and the palea lemma of tassels in maize. Various changes in phenotype are of interest including modifying the plant nutrient profiles, such as altering the fatty acid and oil composition, altering the starch or carbohydrate profile, altering the amino acid content, altering the vitamin content, altering the content of other essential/beneficial secondary products of the plant tissue, and the like. Other phenotypes include the modification of plant growth, regulation, the enhancement of plant disease or pest resistance, improved attraction of beneficial organisms, improved repulsion of deleterious organisms, and the like. These results can be achieved by providing expression of heterologous or increased expression of endogenous products in the plant. Alternatively, the results can be achieved by providing for a reduction of expression of one or more endogenous products, particularly enzymes or cofactors in the plant. These changes result in a change in phenotype of the transformed plant.

Genes of interest are reflective of the commercial markets and interests of those involved in the development of the crop. Crops and markets of interest change, and as developing nations open up world markets, new crops and technologies will emerge also. In addition, as our understanding of agronomic traits and characteristics such as yield and heterosis increase, the choice of genes for transformation will change accordingly. General categories of genes of interest include, for example, those genes involved in information, such as zinc fingers, those involved in communication, such as kinases, and those involved in housekeeping, such as heat shock proteins. More specific categories of transgenes, for example, include genes encoding important traits for agronomics, insect resistance, disease resistance, herbicide resistance, sterility, grain characteristics, and commercial products. Genes of interest include, generally, those involved in oil, starch, carbohydrate, or nutrient metabolism as well as those affecting kernel size, sucrose loading, and the like.

Agronomically important traits such as oil, starch, and protein content can be genetically altered in addition to using traditional breeding methods. Modifications include increasing content of oleic acid, saturated and unsaturated oils, increasing levels of lysine and sulfur, providing essential amino acids, and also modification of starch. Hordothionin protein modifications are described in U.S. application Ser. No. 08/838,763, filed Apr. 10, 1997, now U.S. Pat. No. 5,990,389; and U.S. Pat. Nos. 5,703,049, 5,885,801, and 5,885,802, herein incorporated by reference. Another example is lysine and/or sulfur rich seed protein encoded by the soybean 2S albumin described in U.S. Pat. No. 5,850,016, and the chymotrypsin inhibitor from barley, described in Williamson et al. (1987) *Eur. J. Biochem.* 165:99–106, the disclosures of which are herein incorporated by reference.

Derivatives of the coding sequences can be made by site-directed mutagenesis to increase the level of preselected amino acids in the encoded polypeptide. For example, the gene encoding the barley high lysine polypeptide (BHL) is derived from barley chymotrypsin inhibitor, U.S. application Ser. No. 08/740,682, filed Nov. 1, 1996, and WO 98/20133, the disclosures of which are herein incorporated by reference. Other proteins include methionine-rich plant proteins such as from sunflower seed (Lilley et al. (1989) *Proceedings of the World Congress on Vegetable Protein Utilization in Human Foods and Animal Feedstuffs*, ed. Applewhite (American Oil Chemists Society, Champaign, Ill.), pp. 497–502; herein incorporated by reference); corn (Pedersen et al. (1986) *J. Biol. Chem.* 261:6279; Kirihara et al. (1988) *Gene* 71:359; both of which are herein incorporated by reference); and rice (Musumura et al. (1989) *Plant Mol. Biol.* 12:123, herein incorporated by reference). Other agronomically important genes encode latex, Floury 2, growth factors, seed storage factors, and transcription factors.

Insect resistance genes may encode resistance to pests that have great yield drag such as rootworm, cutworm, European Corn Borer, and the like. Such genes include, for example, *Bacillus thuringiensis* toxic protein genes (U.S. Pat. Nos. 5,366,892; 5,747,450; 5,737,514; 5,723,756; 5,593,881; and Geiser et al. (1986) *Gene* 48:109); lectins (Van Damme et al. (1994) *Plant Mol. Biol.* 24:825); and the like.

Genes encoding disease resistance traits include detoxification genes, such as against fumonosin (U.S. Pat. No. 5,792,931); avirulence (avr) and disease resistance (R) genes (Jones et al. (1994) *Science* 266:789; Martin et al. (1993) *Science* 262:1432; and Mindrinos et al. (1994) *Cell* 78:1089); and the like.

The quality of grain is reflected in traits such as levels and types of oils, saturated and unsaturated, quality and quantity of essential amino acids, and levels of cellulose. In corn, modified hordothionin proteins are described in U.S. application Ser. No. 08/838,763, filed Apr. 10, 1997, now U.S. Pat. No. 5,990,389, and U.S. Pat. Nos. 5,703,049, 5,885,801, and 5,885,802.

Commercial traits can also be encoded on a gene or genes that could increase for example, starch for ethanol production, or provide expression of proteins. Another important commercial use of transformed plants is the production of polymers and bioplastics such as described in U.S. Pat. No. 5,602,321. Genes such as β-Ketothiolase, PHBase (polyhydroxyburyrate synthase), and acetoacetyl-CoA reductase (see Schubert et al. (1988) *J. Bacteriol.* 170:5837–5847) facilitate expression of polyhyroxyalkanoates (PHAs).

Exogenous products include plant enzymes and products as well as those from other sources including procaryotes and other eukaryotes. Such products include enzymes, cofactors, hormones, and the like. The level of proteins, particularly modified proteins having improved amino acid distribution to improve the nutrient value of the plant, can be increased. This is achieved by the expression of such proteins having enhanced amino acid content.

As noted, the heterologous nucleotide sequence operably linked to a promoter disclosed herein to form the promoter-driven construct may be an antisense sequence for a targeted gene. By "antisense DNA nucleotide sequence" is intended a sequence that is in inverse orientation to the 5'-to-3' normal orientation of that nucleotide sequence. When delivered into a plant cell, expression of the antisense DNA sequence prevents normal expression of the DNA nucleotide sequence for the targeted gene. The antisense nucleotide sequence encodes an RNA transcript that is complementary to and capable of hybridizing to the endogenous messenger RNA (mRNA) produced by transcription of the DNA nucleotide sequence for the targeted gene. In this case, production of the native protein encoded by the targeted gene is inhibited to achieve a desired phenotypic response. Thus, the promoter-driven constructs may comprise antisense DNA sequences to reduce or inhibit expression of a native protein in the plant tissue of interest. It is recognized that modifications of the antisense sequences may be made as long as the sequences hybridize to and interfere with expression of the corresponding MRNA. In this manner, antisense constructions having 70%, preferably 80%, more preferably 85% sequence identity to the corresponding antisensed sequences may be used. Furthermore, portions of the antisense nucleotides may be used to disrupt the expression of the target gene. Generally, sequences of at least 50 nucleotides, 100 nucleotides, 200 nucleotides, or greater may be used.

The nucleotide sequences for the promoters may be operably linked with a nucleotide sequence whose expression is to be controlled to achieve a desired phenotypic response. By "operably linked" is intended the transcription or translation of the heterologous nucleotide sequence is under the influence of the promoter sequence. In this manner, the nucleotide sequences for the promoters operably linked to a heterologous nucleotide sequence of interest may be provided in promoter-driven constructs or expression cassettes for expression in the plant of interest. For the purposes of this invention promoter-driven constructs and expression cassettes are used interchangeably.

Such expression cassettes will comprise a transcriptional initiation region, such as the small synthetic promoter Rsyn7, operably linked to the nucleotide sequence whose expression is to be controlled. Such an expression cassette is provided with a plurality of restriction sites for insertion of the nucleotide sequence to be under the transcriptional regulation of the regulatory regions. The expression cassette may additionally contain selectable marker genes.

The promoter-driven construct or expression cassette will include in the 5'-to-3' direction of transcription, a transcriptional and translational initiation region, include sequences encoding introns (but not absolutely required), a heterologous nucleotide sequence of interest, and a transcriptional and translational termination region functional in plants. The termination region may be native with the transcriptional initiation region comprising one of the promoter nucleotide sequences of the present invention, may be native with the DNA sequence of interest, or may be derived from another source. Convenient termination regions are available from the Ti-plasmid of *A. tumefaciens,* such as the octopine synthase and nopaline synthase termination regions. See also, Guerineau et al. (1991) *Mol. Gen. Genet.* 262:141–144; Proudfoot (1991) *Cell* 64:671–674; Sanfacon et al. (1991) *Genes Dev.* 5:141–149; Mogen et al. (1990) *Plant Cell* 2:1261–1272; Munroe et al. (1990) *Gene* 91:151–158; Ballas et al. (1989) *Nucleic Acids Res.* 17:7891–7903; Joshi et al. (1987) *Nucleic Acid Res.* 15:9627–9639.

In accordance with the present invention the expression cassette comprising the elements described above will additionally contain a matrix attachment region (MAR) DNA sequence located at the 5' end of the transcription initiation region, or at the 3' end of the translational termination region, or preferably at both the 5' and the 3' ends of the expression cassette or promoter-driven construct.

The expression cassette comprising a promoter sequence operably linked to a heterologous nucleotide sequence may also contain at least one additional nucleotide sequence for a gene to be cotransformed into the organism. Alternatively, the additional sequence(s) can be provided on another expression cassette.

Where appropriate, the heterologous nucleotide sequence of interest operably linked and under the control of a promoter may be optimized for enhanced expression in the transformed plant. That is, these nucleotide sequences can be synthesized using plant-preferred codons for improved expression. Methods are available in the art for synthesizing plant-preferred nucleotide sequences. See, for example, U.S. Pat. Nos. 5,380,831, 5,436,391, and Murray et al. (1989) *Nucleic Acids Res.* 17:477–498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The promoter constructs or expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Natl. Acad. Sci. USA* 86:6126–6130); potyvirus leaders, for example, TEV leader (Tobacco Etch Virus) (Allison et al. (1986)); MDMV leader (Maize Dwarf Mosaic Virus) (*Virology* 154:9–20); human immunoglobulin heavy-chain binding protein (BiP) (Macejak and Sarnow (1991) *Nature* 353:90–94); untranslated leader from the coat protein mRNA of alfalfa mosaic virus (AMV RNA 4) (Jobling and Gehrke (1987) *Nature* 325:622–625); tobacco mosaic virus leader (TMV) (Gallie et al. (1989) *Molecular Biology of RNA,* pages 237–256); and maize chlorotic mottle virus leader (MCMV) (Lommel et al. (1991) *Virology* 81:382–385). See also Della-Cioppa et al. (1987) *Plant Physiol.* 84:965–968. Other methods known to enhance translation can also be utilized, for example, introns, and the like.

The expression cassette may contain one or more than one gene or nucleic acid sequence to be transferred and expressed in the transformed plant. Alternatively, multiple expression cassettes, each comprising MAR sequences when so desired, may be provided.

Generally, the expression cassette will comprise a selectable or screenable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, and 2,4-dichlorophenoxyacetate (2,4-D). See generally, Yarranton (1992) *Curr. Opin. Biotech.* 3:506–511; Christopherson et al. (1992) *Proc. Natl. Acad Sci. USA* 89:6314–6318; Yao et al. (1992) *Cell* 71:63–72; Reznikoff (1992) *Mol. Microbiol.* 6:2419–2422; Barkley et al. (1980) *The Operon* pp. 177–220; Hu et al. (1987) *Cell* 48:555–566; Brown et al. (1987) *Cell* 49:603–612; Figge et al. (1988) *Cell* 52:713–722; Deuschle et al. (1989) *Proc. Natl. Acad. Sci. USA* 86:5400–5404; Fuerst et al. (1989) *Proc. Natl. Acad. Sci. USA* 86:2549–2553; Deuschle et al. (1990) *Science* 248:480–483; Gossen (1993) Ph.D Thesis, University of Heidelberg; Reines et al. (1993) *Proc. Natl. Acad. Sci. USA* 90:1917–1921; Labow et al. (1990) *Mol. Cell. Biol.* 10:3343–3356; Zambretti et al. (1992) *Proc. Natl. Acad. Sci. USA* 89:3952–3956; Baim et al. (1991) *Proc. Natl. Acad. Sci. USA* 88:5072–5076; Wyborski et al. (1991) *Nuc. Acids Res.* 19:4647–4653; Hillenand-Wissman (1989) *Topics in Mol. and Struc. Biol.* 10:143–162; Degenkolb et al. (1991) *Antimicrob. Agents Chemother.* 35:1591–1595; Kleinschnidt et al. (1988) *Biochemistry* 27:1094–1104; Gatz et al. (1992) *Plant J.* 2:397–404; Bonin (1993) Ph.D Thesis, University of Heidelberg; Gossen et al. (1992) *Proc. Natl. Acad. Sci. USA* 89:5547–5551; Oliva et al. (1992) *Antimicrob. Agents Chemother.* 36:913–919; Hlavka et al. (1985) *Handbook of Exp. Pharmacology* 78; Gill et al. (1988) *Nature* 334:721–724. Such disclosures are herein incorporated by reference.

The above list of selectable marker genes are not meant to be limiting. Any marker gene can be used in the present invention.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resection, ligation, PCR, or the like may be employed, where insertions, deletions or substitutions, e.g transitions and transversions, may be involved.

The various fragments comprising the DNA construct (promoters, nucleotide sequences of interest, terminators, markers, and the like) may be introduced consecutively into an appropriate transformation vector by restriction enzyme cleavage of the vector and insertion of the particular fragment into the available site. By appropriate transformation vector is intended Agrobacterium-based vectors, non-Agrobacterium-based vectors, ballistic vectors, and vectors suitable for DNA-mediated transformation. More preferably, the vector will be a plasmid designed with a pair of unique restriction enzyme sites that flank the ends of the DNA construct. By pair of unique restriction enzyme sites is intended two recognition sites for a restriction enzyme, said sites not occurring elsewhere within the backbone of the transformation vector or within the DNA construct. This flanking pair of unique restriction sites is selected and designed into the transformation vector, which is used for assembly of the DNA construct, to allow for intact isolation of the entire DNA construct as a linear fragment that is incapable of recircularizing by end-joining of the overhangs. All of these techniques are well known in the art and are particularly presented in Sambrook et al. (1989) *Molecular Cloning: A Laboratory Manual* ($2^{nd}$ ed.; Cold Spring Harbor Laboratory: Cold Spring Harbor, N.Y., herein incorporated by reference.

The DNA construct of the present invention comprising a promoter region, a heterologous nucleotide sequence, transcription and translational initiation regions and transcription and translational termination regions, flanked at the 5' and 3' ends by MAR elements can be introduced into the genome of the desired plant host with a variety of techniques known in the art. In this manner, genetically modified plants, plant cells, plant tissue, seed, and the like can be obtained. The transformation vector and hence method of transformation chosen will depend on the type of plant or plant cell, i.e. monocot or dicot, targeted for transformation.

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4:320–334), electroporation (Riggs et al. (1986) *Proc. Natl. Acad. Sci. USA* 83:5602–5606, Agrobacterium-mediated transformation (Townsend et al., U.S. Pat. No. 5,563,055), direct gene transfer (Paszkowski et al. (1984) *EMBO J.* 3:2717–2722), and ballistic particle acceleration (see, for example, Sanford et al., U.S. Pat. No. 4,945,050; Tomes et al., U.S. Pat. No. 5,879,918; Tomes et al., U.S. Pat. No. 5,886,244; Bidney et al., U.S. Pat. No. 5,932,782; Tomes et al. (1995) "Direct DNA Transfer into Intact Plant Cells via Microprojectile Bombardment," in *Plant Cell, Tissue, and Organ Culture: Fundamental Methods,* ed. Gamborg and Phillips (Springer-Verlag, Berlin); and McCabe et al. (1988) *Biotechnology* 6:923–926). Also see Weissinger et al. (1988) *Ann. Rev. Genet.* 22:421–477; Sanford et al. (1987) *Particulate Science and Technology* 5:27–37 (onion); Christou et al. (1988) *Plant Physiol.* 87:671–674 (soybean); McCabe et al. (1988) *Bio/Technology* 6:923–926 (soybean); Finer and McMullen (1991) *In Vitro Cell Dev. Biol.* 27P:175–182 (soybean); Singh et al. (1998) *Theor. Appl. Genet.* 96:319–324 (soybean); Datta et al. (1990) *Biotechnology* 8:736–740 (rice); Klein et al. (1988) *Proc. Natl. Acad. Sci. USA* 85:4305–4309 (maize); Klein et al. (1988) *Biotechnology* 6:559–563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in *Plant Cell, Tissue, and Organ Culture: Fundamental Methods,* ed. Gamborg (Springer-Verlag, Berlin) (maize); Klein et al. (1988) *Plant Physiol.* 91:440–444 (maize); Fromm et al. (1990) *Biotechnology* 8:833–839 (maize); Hooykaas-Van Slogteren et al. (1984) *Nature (London)* 311:763–764; Bowen et al., U.S. Pat. No. 5,736,369 (cereals); Bytebier et al. (1987) *Proc. Natl. Acad. Sci. USA* 84:5345–5349 (Liliaceae); De Wet et al. (1985) in *The Experimental Manipulation of Ovule Tissues,* ed. Chapman et al. (Longman, N.Y.), pp. 197–209 (pollen); Kaeppler et al. (1990) *Plant Cell Reports* 9:415–418 and Kaeppler et al. (1992) *Theor. Appl. Genet.* 84:560–566 (whisker-mediated transformation); D'Halluin et al. (1992) *Plant Cell* 4:1495–1505 (electroporation); Li et al. (1993) *Plant Cell Reports* 12:250–255 and Christou and Ford (1995) *Annals of Botany* 75:407–413 (rice); Osjoda et al. (1996) *Nature Biotechnology* 14:745–750 (maize via *Agrobacterium tumefaciens*); all of which are herein incorporated by reference.

Following transformation of plant cells, regeneration of fertile transformed plants can be accomplished using an appropriate method for the plant host chosen from a variety of procedures well known in the art. See, for example, McCormick et al. (1986) *Plant Cell Reports* 5:81–84, herein incorporated by reference. These plants may then be grown, and either pollinated with the same transformed strain or different strains, and the resulting hybrid having the desired phenotypic characteristic identified. Two or more generations may be grown to ensure that the subject phenotypic characteristic is stably maintained and inherited and then seeds harvested to ensure the desired phenotype or other property has been achieved.

The present invention may be used for transformation of any plant species, including, but not limited to, corn (*Zea mays*), Brassica sp. (e.g., *B. napus, B. rapa, B. juncea*), particularly those Brassica species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (Cofea spp.), coconut (*Cocos nucifera*), pineapple (*Ananas comosus*), citrus trees (Citrus spp.), cocoa (*Theobroma cacao*), tea (*Camellia sinensis*), banana (Musa spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (Saccharum spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (Lathyrus spp.), and members of the genus Cucumis such as cucumber (*C. sativus*), cantaloupe (*C. cantalupensis*), and musk melon (*C. melo*). Ornamentals include azalea (Rhododendron spp.), hydrangea (*Macrophylla hydrangea*), hibiscus (*Hibiscus rosasanensis*), roses (Rosa spp.), tulips (Tulipa spp.), daffodils (Narcissus spp.), petunias (*Petunia hybrida*), carnation (*Dianthus caryophyllus*), poinsettia (*Euphorbia pulcherrima*), and chrysanthemum. Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Preferably, plants of the present invention are crop plants (for example, corn, alfalfa, sunflower, Brassica, soybean, cotton, safflower, peanut, sorghum, wheat, millet, tobacco, etc.), more preferably corn and soybean plants, yet more preferably corn plants.

The following experiments are offered by way of illustration and not by way of limitation.

EXPERIMENTAL

EXAMPLE 1
Transformation of Maize With Promoter::GUS Constructs

The 5' flanking region of the maize ADH1-s gene was previously shown to harbor MAR/SAR-like activity based on in vitro binding (Avramova, Z. and J. L. Bennetzen (1993) *PMB* 22:1135–1143; Avramova, Z. et al. (1995) *Plant Cell* 7:1667–1680), in vivo hyperactivity to osmium tetroxide (A. L. Paul, R. J. Ferl, *PMB* 22:1145–1151 (1993), effects on gene expression in transgenic cell lines (shown above). Using two promoter:GUS constructs with different transgenic expression patterns, the effects of flanking these GUS genes with the maize 5' ADH1 MARS/SARS were observed on their expression patterns and levels in transgenic maize. The two constructs used included a synthetic promoter:GUS, that confers nearly constitutive activity throughout transgenic maize plants and the wheat peroxidase:GUS that predominantly limits high levels of GUS activity in root tissue of transgenic maize. A diagram showing the fragment from the plasmid PHP7917 containing MAR flanked Rsyn7:GUS construct is given in FIG. 1.

MAR-flanked promoter-driven constructs were introduced into immature maize embryos via particle bombardment at two doses with MARS-flanked selectable marker construct. Constructs without MARS elements were co-bombarded with a selectable marker gene also without MARS-flanking sequences. One T0 plant from each of the 7–8 actively expressing lines for each construct was measured for GUS activity both quantitatively as well as histochemically in various tissues. Table 1 refers to the plasmids with the promoter-driven GUS constructs with and without MAR elements.

TABLE 1

| GUS Constructs. | | | |
|---|---|---|---|
| Plasmid | Promoter | No MARS | +MARS |
| 5909 | Ta Perox | X | |
| 6806 | Rsyn7 | X | |
| 7916 | Ta Perox | | X |
| 7917 | Rsyn7 | | X |

Immature maize embryos from greenhouse donor plants are bombarded with a plasmid containing the Rsyn7 promoter operably linked to a nulceotide sequence encoding the GUS reporter protein flanked by MAR elements, and a selectable marker gene, such as PAT (Wohlleben et al. (1988) *Gene* 70:25–37) that confers resistance to the herbicide Bialaphos. Transformation is performed as follows. All media recipes are in the Appendix.

Preparation of Target Tissue

The ears are surface sterilized in 30% Chlorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned with the 2.5-cm target zone in preparation for bombardment.

Preparation of DNA

A plasmid vector comprising a heterologous gene of interest operably linked to a promoter sequence of the present invention is constructed. An expression cassette containing a heterologous gene of interest operably linked to the promoter sequences was cloned into a transformation vector comprising a PAT selectable marker gene. Plasmid DNA is precipitated onto 1.1 μm (average diameter) tungsten pellets using a $CaCl_2$ precipitation procedure as follows:

100 μl prepared tungsten particles in water

10 μl (1 μg) DNA in TrisEDTA buffer (1 μg total)

100 μl 2.5 M $CaCl_2$

10 μl 0.1 M spermidine

Each reagent is added sequentially to the tungsten particle suspension, and mixed on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 μl 100% ethanol is added to the final tungsten particle pellet. For particle gun bombardment, the tungsten/DNA particles are briefly sonicated and 10 μl spotted onto the center of each macrocarrier and allowed to dry about 2 minutes before bombardment.

Particle Gun Treatment

The sample plates are bombarded at level #4 in particle gun #HE34-1 or #HE34-2. All samples receive a single shot at 650 PSI, with a total often aliquots taken from each tube of prepared particles/DNA.

Subsequent Treatment

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration.

Following somatic embryo maturation (2–4 weeks), well-developed somatic embryos are transferred to medium for germination and transferred to the lighted culture room. Approximately 7–10 days later, developing plantlets are transferred to 272V hormone-free medium in tubes for 7–10 days until plantlets are well established. Plants are then transferred to inserts in flats (equivalent to 2.5" pot) containing potting soil and grown for 1 week in a growth chamber, subsequently grown an additional 1–2 weeks in the greenhouse, then transferred to classic 600 pots (1.6 gallon) and grown to maturity. Plants are monitored and scored for GUS activity.

EXAMPLE 2

Figure 2A:
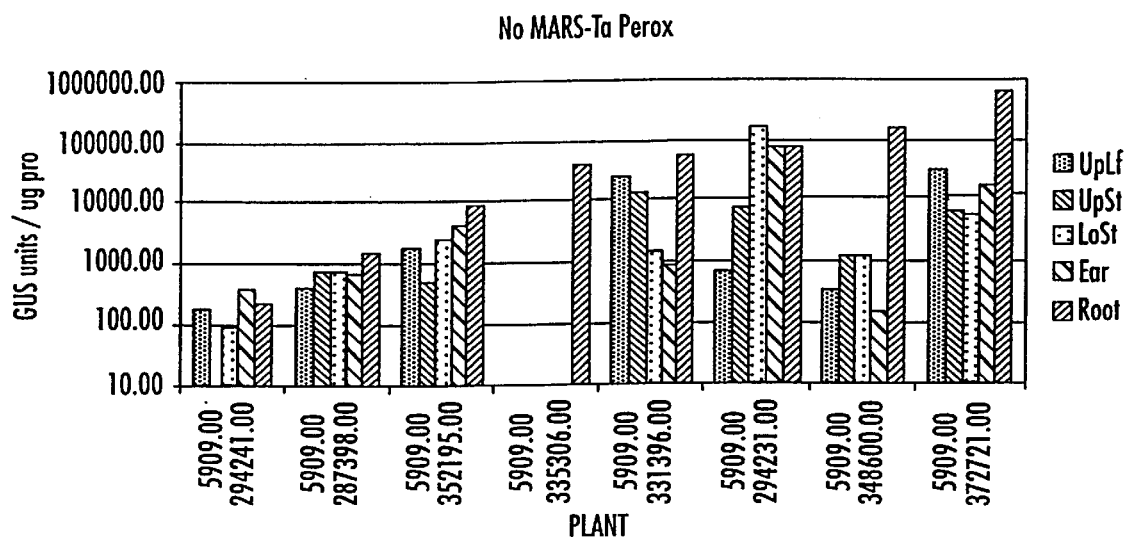
FIG. 2 shows the effect of MAR elements on GUS expression of a Ta Peroxidase promoter. The abbreviations are as follows: UpLf (upper leaf); UpSt (upper stem); LoSt (lower stem); pro (protein).
Figure 2B:
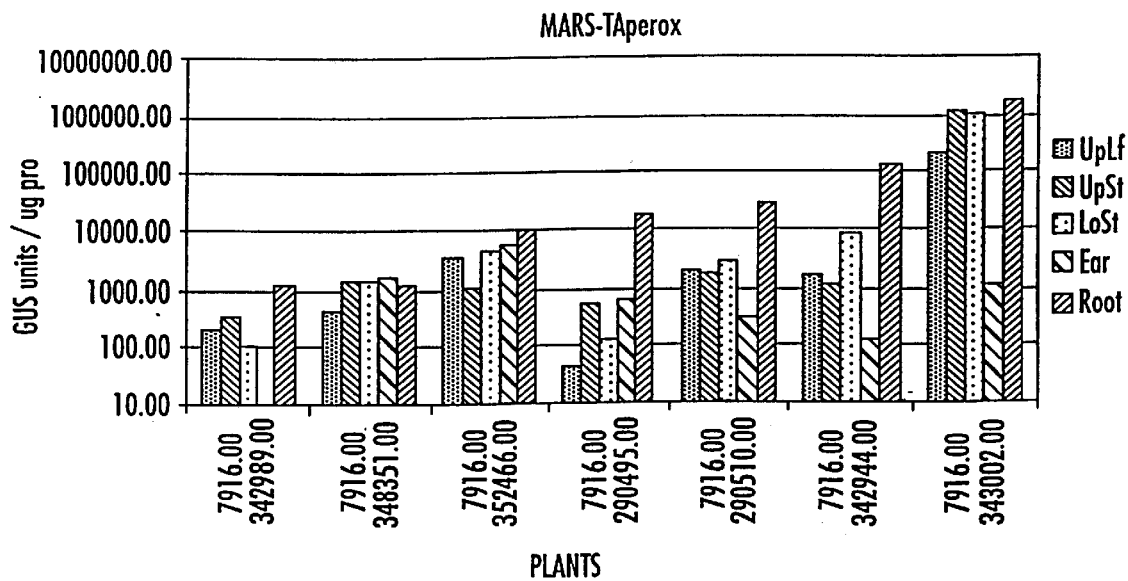

Effect of MAR Elements on GUS Expression of Ta Peroxidase Promoter in Transgenic Maize Various tissues (as indicated) from VT-staged to maize plants from independent events were harvested and measured for GUS activity. The data are sorted with ascending root activity. Overall the ADH1 5' MAR element contributed little to increasing activity levels and did not affect the TA peroxidase promoter site of expression in any dramatic way. See FIG. 2.

EXAMPLE 3

Figure 3A:
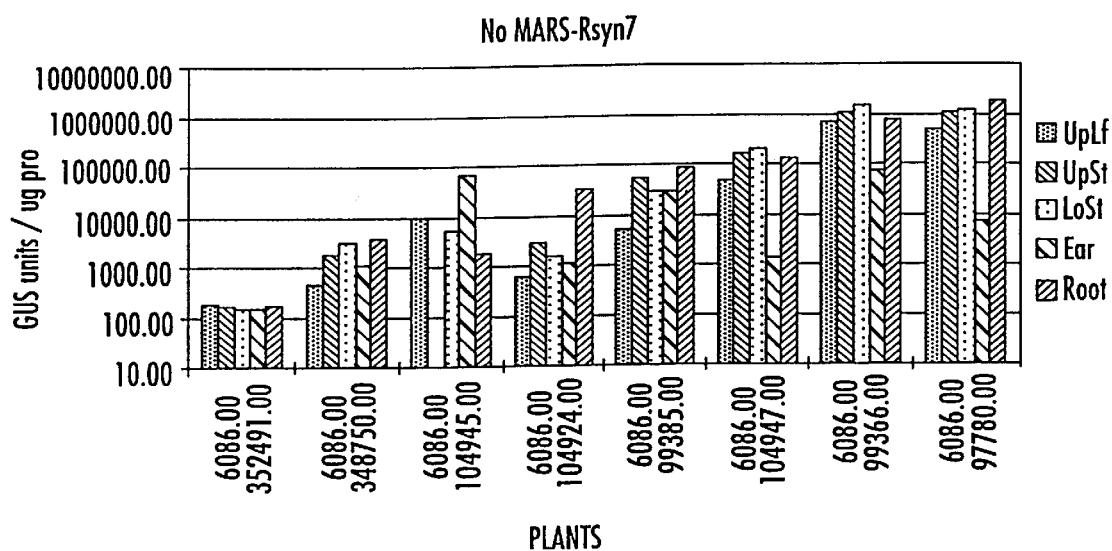
FIG. 3 shows the effect of MAR elements on the Rsyn7 promoter (SEQ ID NOs: 1, 2, and 3). The abbreviations are the same as those in FIG. 2.
Figure 3B:
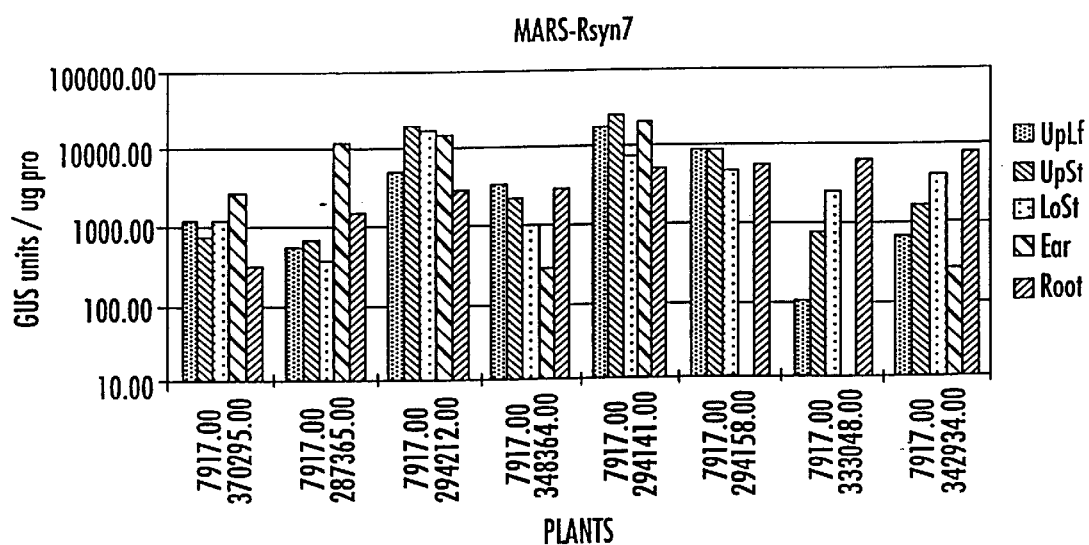

Effects of MAR Elements on the Small Synthetic Promoter, Rsyn7, in Various Tissues of T0 Transgenic Maize Tissues were harvested and processed as described in Example 2. The data was sorted with ascending root activity. Based on histochemical data, the No-MAR-Rsyn7 shows generally high constitutive activity. The MAR-Rsyn7 showed a significant reduction in overall activity (note scale differences between the two graphs). Much of the differences seen between the MAR- and the No-MAR-Rsyn7 was observed in the histochemical staining whereby the predominate activity due to the presence of the MAR sequences occurs in the cortical/epidermal cell sites as lateral root emerging sites, less activity in leaf/stems and more activity detected in the glumes of developing ears. These staining patterns were observed in 6/8 of the mature T0 plant events assayed. See FIG. 3.

The effect on the constitutive Rsyn7:GUS was more striking in the histochemical staining analysis resulting in limited but intense expression at lateral root emerging sites of primary and adventitious roots and strong expression in the glumes of the developing kernel as well as the kernel pericarp with much less expression elsewhere in the aerial portion of the plant.

Appendix

272 V

| Ingredient | Amount | Unit |
| --- | --- | --- |
| D-I $H_2O$ | 950.000 | Ml |
| MS Salts (GIBCO 11117-074) | 4.300 | G |
| Myo-Inositol | 0.100 | G |
| MS Vitamins Stock Solution ## | 5.000 | Ml |
| Sucrose | 40.000 | G |
| Bacto-Agar @ | 6.000 | G |

Directions:

@ = Add after bringing up to volume

Dissolve ingredients in polished D-I $H_2O$ in sequence

Adjust to pH 5.6

Bring up to volume with polished D-I $H_2O$ after adjusting pH

Sterilize and cool to 60° C.

## = Dissolve 0.100 g of Nicotinic Acid; 0.020 g of Thiamine.HCL; 0.100 g of Pyridoxine.HCL; and 0.400 g of Glycine in 875.00 ml of polished D-I $H_2O$ in sequence. Bring up to volume with polished D-I $H_2O$. Make in 400 ml portions. Thiamine.HCL & Pyridoxine.HCL are in Dark Desiccator. Store for one month, unless contamination or precipitation occurs, then make fresh stock.

Total Volume (L) = 1.00

288 J

| Ingredient | Amount | Unit |
| --- | --- | --- |
| D-I $H_2O$ | 950.000 | Ml |
| MS Salts | 4.300 | G |
| Myo-Inositol | 0.100 | G |
| MS Vitamins Stock Solution ## | 5.000 | Ml |
| Zeatin .5 mg/ml | 1.000 | Ml |
| Sucrose | 60.000 | G |
| Gelrite @ | 3.000 | G |
| Indoleacetic Acid 0.5 mg/ml # | 2.000 | Ml |
| 0.1 mM Abscisic Acid | 1.000 | Ml |
| Bialaphos 1 mg/ml # | 3.000 | Ml |

Directions:

@ = Add after bringing up to volume

Dissolve ingredients in polished D-I $H_2O$ in sequence

Adjust to pH 5.6

Bring up to volume with polished D-I $H_2O$ after adjusting pH

Sterilize and cool to 60° C.

Add 3.5 g/L of Gelrite for cell biology.

Dissolve 0.100 g of Nicotinic Acid; 0.020 g of Thiamine.HCL; 0.100 g of Pyridoxine.HCL; and 0.400 g of Glycine in 875.00 ml of polished D-I $H_2O$ in sequence. Bring up to volume with polished D-I $H_2O$. Make in 400 ml portions. Thiamine.HCL & Pyridoxine.HCL are in Dark Desiccator. Store for one month, unless contamination or precipitation occurs, then make fresh stock.

Total Volume (L) = 1.00

560 R

| Ingredient | Amount | Unit |
|---|---|---|
| D-I Water, Filtered | 950.000 | Ml |
| CHU (N6) Basal Salts (SIGMA C-1416) | 4.000 | G |
| Eriksson's Vitamin Mix (1000X SIGMA-1511 | 1.000 | Ml |
| Thiamine.HCL 0.4 mg/ml | 1.250 | Ml |
| Sucrose | 30.000 | G |
| 2,4-D 0.5 mg/ml | 4.000 | Ml |
| Gelrite @ | 3.000 | G |
| Silver Nitrate 2 mg/ml # | 0.425 | Ml |
| Bialaphos 1 mg/ml # | 3.000 | Ml |

Directions:
@ = Add after bringing up to volume
# = Add after sterilizing and cooling to temp.
Dissolve ingredients in D-I H$_2$O in sequence
Adjust to pH 5.8 with KOH
Bring up to volume with D-I H$_2$O
Sterilize and cool to room temp.
Total Volume (L) = 1.00

560 Y

| Ingredient | Amount | Unit |
|---|---|---|
| D-I Water, Filtered | 950.000 | Ml |
| CHU (N6) Basal Salts (SIGMA C-1416) | 4.000 | G |
| Eriksson's Vitamin Mix (1000X SIGMA-1511 | 1.000 | Ml |
| Thiamine.HCL 0.4 mg/ml | 1.250 | Ml |
| Sucrose | 120.000 | G |
| 2,4-D 0.5 mg/ml | 2.000 | Ml |
| L-Proline | 2.880 | G |
| Gelrite @ | 2.000 | G |
| Silver Nitrate 2 mg/ml # | 4.250 | Ml |

Directions:
@ = Add after bringing up to volume
# = Add after sterilizing and cooling to temp.
Dissolve ingredients in D-I H$_2$O in sequence
Adjust to pH 5.8 with KOH
Bring up to volume with D-I H$_2$O
Sterilize and cool to room temp.
Autoclave less time because of increased sucrose
Total Volume (L) = 1.00

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed:

1. A DNA construct comprising a promoter-driven construct wherein said promoter-driven construct comprises:
   (a) an Rsyn7 promoter comprising the nucleotide sequence set forth in SEQ ID NO: 1 or 2;
   (b) a nucleotide sequence operably linked to said promoter;
   (c) a transcription and translation termination region; and
   (d) maize ADH1 matrix attachment region DNA sequences flanking the combined elements (a), (b), and (c).

2. The DNA construct of claim 1 wherein said Rsyn7 promoter further comprises an upstream element having the sequence set forth in SEQ ID NO:3.

3. A plant having stably incorporated into its genome the DNA construct of claim 1.

4. A plant cell having stably incorporated into its genome the DNA construct of claim 1.

5. The plant of claim 3, wherein said plant is a monocot.

6. The plant of claim 3, wherein said plant is a dicot.

7. Transformed seed of the plant of claim 3.

8. The plant cell of claim 4, wherein said plant cell is from a monocotyledonous plant.

9. The plant cell of claim 4, wherein said plant cell is from a dicotyledonous plant.

10. The plant of claim 5, wherein said monocot is maize.

11. The plant cell of claim 8, wherein said monocotyledonous plant is maize.

12. A method for altering the expression pattern of an Rsyn7 promoter construct, said method comprising operably linking at least one maize ADH1 matrix attachment region to said construct, said construct comprising an Rsyn7 promoter comprising the sequence set forth in SEQ ID No: 1 or 2, a heterologous DNA sequence operably linked to said promoter, and a transcription and translation termination region, wherein said matrix attachment region alters the expression pattern of said promoter.

13. The method of claim 12, wherein said Rsyn7 promoter further comprises an upstream element having the sequence set forth in SEQ ID NO:3.

14. A DNA construct comprising the following operably linked elements:
   (a) an Rsyn7 promoter comprising the nucleotide sequence set forth in SEQ ID NO: 1 or 2;
   (b) a nucleotide sequence of interest;
   (c) a transcription and translation termination region; and,
   (d) at least one maize ADH1 matrix attachment region DNA sequence.

15. The DNA construct of claim 14, wherein said construct comprises one matrix attachment region DNA sequence 5' to said Rsyn7 promoter.

16. The DNA construct of claim 14, wherein said construct comprises one matrix attachment region DNA sequence 3' to said termination region.

17. The DNA construct of claim 14 wherein said Rsyn7 promoter further comprises an upstream element having the sequence set forth in SEQ ID NO:3.

18. A plant having stably incorporated into its genome a DNA construct comprising the following operably linked elements:
   (a) an Rsyn7 promoter comprising the nucleotide sequence set forth in SEQ ID NO: 1 or 2;
   (b) a nucleotide sequence of interest;
   (c) a transcription and translation termination region; and
   (d) at least one maize ADH1 matrix attachment region DNA sequence.

19. The plant of claim 18, wherein said construct comprises one matrix attachment region DNA sequence 5' to said Rsyn7 promoter.

20. The plant of claim 18, wherein said construct comprises one matrix attachment region DNA sequence 3' to said termination region.

21. The plant of claim 18, wherein said Rsyn7 promoter further comprises an upstream element having the sequence set forth in SEQ ID NO:3.

22. The plant of claim 18, wherein said plant is a monocot.

23. The plant of claim 18, wherein said plant is a dicot.

24. Transformed seed of the plant of claim 18.

25. The plant of claim 21, wherein said plant is a maize.

26. Transformed seed of the plant of claim 22.

* * * * *